US008067217B2

(12) United States Patent
Ueda et al.

(10) Patent No.: US 8,067,217 B2
(45) Date of Patent: Nov. 29, 2011

(54) METHOD FOR PRESERVING REDUCED COENZYME Q10

(75) Inventors: Takahiro Ueda, Takasago (JP); Tadao Ono, Takasago (JP); Shiro Kitamura, Takasago (JP); Yasuyoshi Ueda, Takasago (JP)

(73) Assignee: Kaneka Corporation, Kita-ku, Osaka-shi (JP)

( * ) Notice: Subject to any disclaimer, the term of this patent is extended or adjusted under 35 U.S.C. 154(b) by 376 days.

(21) Appl. No.: 11/315,161

(22) Filed: Dec. 23, 2005

(65) Prior Publication Data
US 2006/0153911 A1    Jul. 13, 2006

Related U.S. Application Data

(60) Provisional application No. 60/651,199, filed on Feb. 10, 2005.

(30) Foreign Application Priority Data

Dec. 28, 2004 (JP) .................................. 2004-379879

(51) Int. Cl.
*C12N 9/98* (2006.01)
(52) U.S. Cl. ................ 435/188; 424/94.3; 568/830
(58) Field of Classification Search .............. 435/188; 424/94.3; 568/830
See application file for complete search history.

(56) References Cited

U.S. PATENT DOCUMENTS

| 6,045,826 | A * | 4/2000 | Borowy-Borowski et al. .................. 424/451 |
| 6,184,255 | B1 | 2/2001 | Mae et al. |
| 7,105,709 | B2 * | 9/2006 | Ueda et al. .................... 568/823 |
| 7,169,590 | B2 * | 1/2007 | Ueda et al. .................... 435/188 |
| 2004/0197418 | A1 | 10/2004 | Ueda et al. |
| 2004/0197886 | A1 | 10/2004 | Ueda et al. |
| 2004/0214301 | A1 | 10/2004 | Ueda et al. |
| 2004/0215040 | A1 | 10/2004 | Ueda et al. |
| 2004/0236154 | A1 | 11/2004 | Ueda et al. |
| 2004/0254403 | A1 | 12/2004 | Ueda et al. |
| 2005/0008630 | A1 | 1/2005 | Ueda et al. |
| 2005/0147598 | A1 | 7/2005 | Ueda et al. |
| 2006/0147542 | A1 * | 7/2006 | Ono et al. ..................... 424/490 |

FOREIGN PATENT DOCUMENTS

| JP | 10-109933 | | 4/1998 |
| JP | 2003-119127 | * | 4/2003 |
| WO | WO 01/52822 | | 7/2001 |
| WO | WO 03/006408 | | 1/2003 |
| WO | WO 03/006409 | | 1/2003 |
| WO | WO 03/006410 | | 1/2003 |
| WO | WO 03/006411 | | 1/2003 |
| WO | WO 03/006412 | | 1/2003 |
| WO | WO 03/008363 | | 1/2003 |
| WO | WO 03/032967 | | 4/2003 |
| WO | WO 03/062182 | | 7/2003 |

OTHER PUBLICATIONS www.yourlifesource.com AIM Cellsparc Q Bulletin, printed Apr. 30, 2008.*
Kommuru T. et al. Stability and Bioequivalence Studies of Two Marketed Formulations of CoQ10 in Beagle Dogs. Chem Pharm Bull (Tokyo) 47(7)1024-1028, 1999.*

* cited by examiner

*Primary Examiner* — Ralph Gitomer
(74) *Attorney, Agent, or Firm* — Connolly Bove Lodge & Hutz LLP

(57) ABSTRACT

The present invention has its object to provide a method for stably preserving a capsule containing reduced coenzyme $Q_{10}$, which is useful as foods, functional nutritive foods, specific health foods, nutritional supplements, nutrients, animal drugs, drinks, feeds, cosmetics, medicines, remedies, preventive drugs, etc. The present invention relates to a method for preserving reduced coenzyme $Q_{10}$ which comprises producing or obtaining a capsule containing reduced coenzyme $Q_{10}$, and controlling environment surrounding the capsule to a relative humidity of not less than 0% but not more than 60%. According to this method, reduced coenzyme $Q_{10}$ can be preserved stably, without requiring huge cost and labor, or special equipment.

11 Claims, No Drawings

METHOD FOR PRESERVING REDUCED COENZYME Q10

This application claims benefit to provisional application 60/651,199 filed Feb. 10, 2005 which is based upon Japan application 2004-379879 filed Dec. 28, 2004.

TECHNICAL FIELD

The present invention relates to a method for preserving reduced coenzyme $Q_{10}$. Reduced coenzyme $Q_{10}$ shows higher oral absorbability as compared with oxidized coenzyme $Q_{10}$ and is a useful compound suited for use in foods, functional nutritive foods, specific health foods, nutritional supplements, nutrients, animal drugs, drinks, feeds, cosmetics, medicines, remedies, preventive drugs, etc.

BACKGROUND ART

Coenzyme Q is an essential constituent widely distributed in living bodies, from bacteria to mammals and is known as a mitochondrial electron transfer system constituent in cells of living bodies. Through repeated oxidation and reduction in mitochondria, coenzymes Q perform their function as transmitter components in the electron transfer system and, further, reduced coenzymes Q are known to have antioxidant activity. In humans, coenzyme $Q_{10}$, whose coenzyme Q side chain comprises 10 repeating structures, is the main component and, generally, about 40 to 90% thereof is present in reduced form in living bodies. The physiological activities of coenzyme Q involve the activation of energy production through mitochondrial activation, activation of cardiac function, stabilizing effect of cell membrane, cell protecting effect through antioxidant activity, and the like.

Oxidized coenzyme $Q_{10}$ is used as a health food in the United States and Europe, and as a medication for congestive heart failure in Japan. In recent years, it has come to be used in Japan as a functional nutritive food. Soft capsules containing oxidized coenzyme $Q_{10}$ predominate especially in the field of health foods and functional nutritive foods.

On the other hand, since reduced coenzyme Q itself has strong antioxidant action, it is possible to effectively increase the antioxidant activity in blood by supplying sufficient quantities of reduced coenzyme Q to blood. Increasing the antioxidant activity in blood is thought to have a wide range of usefulness for many diseases from being aggravated supposedly by active oxygen species, for example, preventing vascular lesions during ischemia-reperfusion, preventing restenosis in arteriosclerosis, preventing vascular lesions following cerebral infarction, preventing arteriosclerosis, preventing complications of diabetes.

It is known that reduced coenzyme $Q_{10}$ can be obtained, for example, by well-known conventional processes such as synthesis, fermentation, extraction from natural sources, and the like, and then concentrating the reduced coenzyme $Q_{10}$ fraction of the effluent resulting from chromatography (Japanese Kokai Publication Hei-10-109933). In this case, as described in the above-cited publication, the chromatographic concentration may be carried out after reduction of oxidized coenzyme $Q_{10}$ contained in the reduced coenzyme $Q_{10}$ with a conventional reducing agent such as sodium borohydride or sodium dithionite, or reduced coenzyme $Q_{10}$ may be prepared by reacting an existing highly pure grade of coenzyme $Q_{10}$ with the reducing agent mentioned above.

Moreover, as a result of intensive research, the present inventors established processes for producing high-quality reduced coenzyme $Q_{10}$, which were disclosed in patent applications (WO03/06408; WO03/06409; WO03/06410; WO03/06411; WO03/06412; WO03/08363; and WO03/32967).

However, reduced coenzyme $Q_{10}$ is readily oxidized to oxidized coenzyme $Q_{10}$ by molecular oxygen, and, even when a high-quality reduced coenzyme $Q_{10}$ is manufactured by a method like the above-mentioned patent applications, it is still an important problem to stabilize reduced coenzyme $Q_{10}$ in processing the same in foods, functional nutritive foods, specific health foods, nutritional supplements, nutrients, animal drugs, drinks, feeds, cosmetics, medicines, remedies, preventive drugs, etc., or raw materials or compositions for the production thereof, and/or to stabilize the same in preserving such products, raw materials or compositions after processing the same. On the occasion of such process and preservation, it is very difficult to completely eliminate or shut out oxygen and, in particular in the step of warming for processing or during long-period preservation of them, the remaining or newcomer oxygen exerts a great adverse influence. This oxidation is directly concerned with such quality problems as the formation of oxidized coenzyme $Q_{10}$ as a byproduct.

Thus, it is a very important problem to stabilize (protect against oxidation) reduced coenzyme $Q_{10}$. To this time, however, few studies have been made on the method and composition for stabilizing coenzyme $Q_{10}$. There are only two examples; one describes a composition comprising a coexisting reducing agent and a method for producing the same (WO01/052822) and, in the other, reduced coenzyme $Q_{10}$ is stabilized in an oil or fat (WO03/062182).

In WO01/052822, there are disclosed 1) a composition comprising an amount, effective in preventing reduced coenzyme $Q_{10}$ from being oxidized to oxidized coenzyme $Q_{10}$, of a reducing agent and an amount, effective in dissolving the reduced coenzyme $Q_{10}$ and reducing agent, of a surfactant or a vegetable oil or a mixture of these, if necessary together with a solvent, 2) a composition for oral administration in the form of gelatin capsule or tablets as prepared from the above composition and, further, 3) a method for preparing the above composition containing reduced coenzyme $Q_{10}$ in situ by using oxidized coenzyme $Q_{10}$ and a reducing agent.

In WO01/052822, however, there is no detailed description of the quality and the stabilizing effect of the reduced coenzyme $Q_{10}$ contained in the above-mentioned compositions, for example. The above-mentioned compositions and the method for preparing the same are very complicated and troublesome so that the compositions may play a plurality of roles (namely the first role as a reaction field for the reduction of oxidized coenzyme $Q_{10}$ to reduced coenzyme $Q_{10}$ and the second role in maintaining reduced coenzyme $Q_{10}$ in a stable condition).

Furthermore, it is noteworthy that the above compositions and/or the method for preparing the same are hard to be referred to as always safe since the reaction mixture is used as such. More specifically, the use of ascorbic acids as a reducing agent in reducing oxidized coenzyme $Q_{10}$ to reduced coenzyme $Q_{10}$ results in the oxidation of the ascorbic acids, leading to the formation of a considerable amount of the corresponding dehydroascorbic acids, which contaminates the above-mentioned compositions. Unlike ascorbic acids, dehydroascorbic acids and the decomposition product oxalic acid are highly harmful. For example, they reportedly cause increases in lipid peroxide level and decreases in antioxidant level in the liver and kidney and increases in oxalic acid level in the kidney, and there is a fear of their producing some adverse effects, for example the effects of decreasing the resistance to oxidative stress and readily causing ureterolithiasis (Nutrition Research, 13, pp 667-676(1993)).

Furthermore, although ascorbic acids are used in WO01/052822, when ascorbic acids are enclosed in a gelatin soft capsule, it is generally known that the disintegration of the gelatin capsule will get worse. Therefore, there is also fear that the absorbability to a living body will be adversely affected in this case.

In WO03/062182, on the other hand, a method for stabilizing reduced coenzyme $Q_{10}$ which is characterized in that reduced coenzyme $Q_{10}$ is admixed in a composition whose main components are oils and fats (except for olive oil) and/or a polyol and which will not substantially interfere with the stabilization of reduced coenzyme $Q_{10}$ is disclosed as a method for protecting reduced coenzyme $Q_{10}$ against oxidation. However, in the above stabilization method, reduced coenzyme $Q_{10}$ could not be preserved stably, for example in the case of being incorporated with sorbitan fatty acid esters and/or polyoxyethylenesorbitan fatty acid esters, because of limitation of materials which could be used.

A method which can preserve reduced coenzyme $Q_{10}$ stably has been searched for under the above situations.

SUMMARY OF THE INVENTION

The present inventors made intensive investigations in an attempt to accomplish the above object and, as a result, surprisingly found that, by preserving a capsule containing reduced coenzyme $Q_{10}$ in a specific condition, reduced coenzyme $Q_{10}$ can be protected against the oxidation. Based on such finding, they have now completed the present invention.

That is, the present invention relates to a method for preserving reduced coenzyme $Q_{10}$ which comprises producing or obtaining a capsule containing reduced coenzyme $Q_{10}$, and controlling environment surrounding the capsule to a relative humidity of not less than 0% but not more than 60%.

The present invention also relates to a packed object wherein a gas controlled to a relative humidity of not less than 0% but not more than 60% and a capsule containing reduced coenzyme $Q_{10}$ are packaged or packed in a packing material.

DETAILED DESCRIPTION OF THE INVENTION

In the following, the present invention is described in detail.

The term "coenzyme $Q_{10}$" used herein means both of reduced one and oxidized one, and, in the case where there are both of them, the above term means the mixture as a whole.

The method for preserving reduced coenzyme $Q_{10}$ of the present invention is characterized in that which comprises producing or obtaining a capsule containing reduced coenzyme $Q_{10}$, and controlling environment surrounding the capsule to a relative humidity of not less than 0% but not more than 60%.

The reduced coenzyme $Q_{10}$ is represented by the formula (1):

$$\underset{\text{OH}}{\underset{|}{\overset{\text{OH}}{\overset{|}{\text{H}_3\text{CO}}}}} \text{CH}_3, (CH_2CH C(CH_3)CH_2)_n H \quad (1)$$

(in which n=10).

The reduced coenzyme $Q_{10}$ that is to be used in the present invention can be produced by a well-known conventional process such as synthesis, fermentation, and extraction from a natural product, for example. More specifically, as is described in Japanese Kokai Publication Hei-10-109933, reduced coenzyme $Q_{10}$ can be produced, for example, by preparing a mixture of oxidized coenzyme $Q_{10}$ and reduced coenzyme $Q_{10}$ by such a known method as synthesis, fermentation or extraction from a natural product and subjecting the mixture to chromatography for the concentration of the reduced coenzyme $Q_{10}$ fraction in the eluate. On that occasion, the oxidized coenzyme $Q_{10}$ coexisting in the reduced coenzyme $Q_{10}$ may be reduced with an ordinary reducing agent such as sodium borohydride or sodium dithionite, followed by concentration by chromatography.

Reduced coenzyme $Q_{10}$ can also be obtained by reacting an existing high purity grade of coenzyme $Q_{10}$ with such a reducing agent as mentioned above. Preferably, reduced coenzyme $Q_{10}$ is obtained by reducing oxidized coenzyme $Q_{10}$ such as an existing high purity grade of coenzyme $Q_{10}$, or a mixture of oxidized coenzyme $Q_{10}$ and reduced coenzyme $Q_{10}$ with an ordinary reducing agent such as sodium dithionite, sodium borohydride or ascorbic acids. More preferably, reduced coenzyme $Q_{10}$ is obtained by reducing oxidized coenzyme $Q_{10}$ such as an existing high purity grade of coenzyme $Q_{10}$, or a mixture of oxidized coenzyme $Q_{10}$ and reduced coenzyme $Q_{10}$ with ascorbic acids.

Now, the capsule containing reduced coenzyme $Q_{10}$ to be used in the present invention is explained.

A capsule containing reduced coenzyme $Q_{10}$ can be produced or obtained as follows, for example.

The capsule containing reduced coenzyme $Q_{10}$ can be obtained, for example, by encapsulating a composition containing reduced coenzyme $Q_{10}$.

The composition containing reduced coenzyme $Q_{10}$ is not particularly restricted provided that it contains reduced coenzyme $Q_{10}$ and may further contain oxidized coenzyme $Q_{10}$.

The upper limit of the content of reduced coenzyme $Q_{10}$ contained in the composition is not particularly restricted but, from the easiness of formulation viewpoint, it is generally 50% by weight, preferably 40% by weight, more preferably 30% by weight, still more preferably 20% by weight relative to the total weight of the composition. The lower limit of the content of reduced coenzyme $Q_{10}$ contained in the composition is not particularly restricted but, from the viewpoint of performing the function of reduced coenzyme $Q_{10}$ effectively and the like viewpoints, it is generally 0.1% by weight, preferably 0.5% by weight, more preferably 1% by weight, still more preferably 3% by weight relative to the total weight of the composition.

The ratio of reduced coenzyme $Q_{10}$ relative to the whole amount of coenzyme $Q_{10}$ (namely the sum of reduced coenzyme $Q_{10}$ and oxidized coenzyme $Q_{10}$) to be used in the present invention is not particularly restricted but, from the viewpoint of performing the function of reduced coenzyme $Q_{10}$ effectively and the like viewpoints, it is for example not lower than 20% by weight, generally not lower than 40% by weight, preferably not lower than 60% by weight, more preferably not lower than 80% by weight, still more preferably not lower than 90% by weight, most preferably not lower than 96% by weight. The upper limit is 100% by weight and although there are no particular limitations, it is generally 99.9% by weight or less.

The weights of reduced coenzyme $Q_{10}$ and oxidized coenzyme $Q_{10}$ referred herein are measured by the method described in the below-mentioned examples.

In the composition containing reduced coenzyme $Q_{10}$, reduced coenzyme $Q_{10}$ may be a crystal, or may be contained in a solution. Needless to say, it may be slurry in which a part of its crystal dissolves.

When reduced coenzyme $Q_{10}$ is contained in a solution or is slurry in which a part of its crystal dissolves, species of fluid components of the composition is not particularly restricted but there may be mentioned, for example, oils and fats, surfactants, ethanol, water and the like fluid substances, and the like. In the present invention, since reduced coenzyme $Q_{10}$ can be stably preserved by controlling environment surrounding the capsule obtained by using the above-mentioned composition to a relative humidity of not less than 0% but not more than 60%, various oils and fats and/or surfactants can be used.

The oils and fats used can be natural oils and fats derived from animals or plants, or synthetic oils and fats or processed oils and fats. Preferably, it is a species permitted for food or medicinal use. As the vegetable oils and fats, there may be mentioned, for example, coconut oil, palm oil, palm kernel oil, linseed oil, camellia oil, brown rice germ oil, rapeseed oil, rice oil, peanut oil, corn oil, wheat germ oil, soybean oil, perillan oil, cotton seed oil, sunflower seed oil, kapok oil, evening primrose oil, shea butter, sal fat, cacao butter, sesame oil, safflower oil, olive oil and the like. As the animal-derived oils and fats, there may be mentioned, forexample, lard, milkfat, fishoils, beef tallowandthe like. Moreover, there may also be mentioned modified oils and fats obtainable by the fractionation, hydrogenation, transesterificaiton, etc. of these natural oils and fats (e.g. hydrogenated oils). It is of course possible to use medium chain fatty acid triglycerides (MCT). Mixtures of these can also be used.

The medium chain fatty acid triglycerides are not particularly restricted but include, for example, triglycerides whose fatty acid-derived moieties each contain 6 to 12 carbon atoms, preferably 8 to 12 carbon atoms, and the like.

Among the oils and fats enumerated above, vegetable oils and fats, synthetic oils and fats, modified oils and fats, and medium chain fatty acid triglycerides, for example, are preferred from the easy handing, odor and the like viewpoints. In selecting these oils and fats, consideration should be given to price of oils and fats, stability and/or solubility of reduced coenzyme $Q_{10}$, and the like. For example, coconut oil, palm oil, palm kernel oil, rape seed oil, rice oil, soy bean oil, cotton seed oil, safflower oil, olive oil, MCT and the like are more preferred, and rice oil, soybean oil, rape seed oil, safflower oil, MCT and the like are still more preferred.

As the surfactants, there may be mentioned, for example, fatty acid partial glycerides, propylene glycol fatty acid esters, phospholipids, sucrose fatty acid esters, sorbitan fatty acid esters, polyoxyethylenesorbitan fatty acid esters, polyglycerol fatty acid esters and the like.

The fatty acid partial glycerides are not particularly restricted but include, for example, monoglycerides and diglycerides derived from fatty acids each containing 6 to 18 carbon atoms, preferably 6 to 12 carbon atoms, and the like.

The propylene glycol fatty acid esters are not particularly restricted but include, for example, monoesters and diesters derived from fatty acids each containing 6 to 18 carbon atoms, preferably 6 to 12 carbon atoms, and the like.

The phospholipids are not particularly restricted but include, for example, egg yolk lecithin, purified soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramide phosphorylethanolamine, ceramide phosphorylglycerol, and mixtures of these, and the like.

As the sucrose fatty acid esters, sorbitan fatty acid esters and polyoxyethylenesorbitan fatty acid esters, there may be mentioned, for example, ones derived from fatty acids each containing 6 or more carbon atoms, preferably 8 or more carbon atoms.

The polyglycerol fatty acid esters are not particularly restricted but include, for example, ones derived from fatty acids each containing preferably 6 or more carbon atoms, particularly preferably 8 or more carbon atoms, and having the degree of polymerization of glycerol of preferably 10 or less, particularly preferably 4 or less.

As the surfactants, particularly preferred are fatty acid partial glycerides, phospholipids, sorbitan fatty acid esters, polyoxyethylene sorbitan fatty acid esters, polyglycerol fatty acid esters and the like.

The substances, which can be coexisted in the composition containing reduced coenzyme $Q_{10}$, are not particularly restricted but include, for example, excipients, disintegrating agents, lubricants, binders, antioxidants, coloring agents, agglutination inhibitors, absorption promoters, dissolution aids for active ingredients, stabilizers, viscosity modifier, and the like. It is of course possible to coexist one or more active components other than coenzyme $Q_{10}$ in the composition.

The excipients are not particularly restricted but include, for example, white soft sugar, lactose, glucose, cornstarch, mannitol, crystalline cellulose, calcium phosphate, calcium sulfate and the like.

The disintegrating agents are not particularly restricted but include, for example, starch, agar, calcium citrate, calcium carbonate, sodium hydrogen carbonate, dextrin, crystalline cellulose, carboxymethylcellulose, tragacanth and the like.

The lubricants are not particularly restricted but include, for example, talc, magnesium stearate, polyethylene glycol, silica, hydrogenated vegetable oils and the like.

The binders are not particularly restricted but include, for example, ethylcellulose, methylcellulose, hydroxypropylmethylcellulose, tragacanth, shellac, gelatin, gum arabic, polyvinylpyrrolidone, polyvinylalcohol, polyacrylic acid, polymethacrylic acid, sorbitol and the like.

The antioxidants are not particularly restricted but include, for example, ascorbic acid, tocopherols, vitarmin A, β-carotene, sodiumhydrogensulfite, sodiumthiosulfate, sodium pyrosulfite, citric acid and the like.

The coloring agents are not particularly restricted but include, for example, ones permitted for addition to pharmaceuticals and foods, and the like.

The agglutination inhibitors are not particularly restricted but include, for example, stearic acid, talc, light anhydrous silicic acid, hydrous silicon dioxide and the like.

The absorption promoters are not particularly restricted but include, for example, higher alcohols, higher fatty acids, the above-mentioned surfactants and the like.

The dissolution aids for active ingredients are not particularly restricted but include, for example, organic acids such as fumaric acid, succinic acid and malic acid, and the like.

The stabilizers are not particularly restricted but include, for example, benzoic acid, sodium benzoate, ethyl parahydroxybenzoate and the like.

The viscosity modifiers are not particularly restricted but include, for example, beeswax, carnauba wax, candelilla wax, rice bran wax, sugarcane wax, shellac wax, jojoba wax and the like. Beeswax, carnauba wax and rice bran wax are preferred, and beeswax is particularly preferred.

As the active components other than coenzyme $Q_{10}$ include, for example, amino acids, vitamins, minerals, polyphenols, organic acids, saccharides, peptides, proteins and the like.

The composition containing reduced coenzyme $Q_{10}$ prepared as mentioned above can be encapsulated by general methods using a soft capsule, a hard capsule, a microcapsule and the like. A soft capsule is preferred.

The materials of the capsule are not particularly restricted but include, for example, gelatin derived from cow bones, cowhide, pig skin, fish skin and the like; substances derived from seaweed such as carrageenan and alginic acid, which can be used as a food additive; substances derived from plant seeds such as locust bean gum and guar gum; manufacturing agents containing cellulose; starch such as wheat starch, potato starch, sweet potato starch, cornstarch and dextrin; and the like.

From the easiness of acquisition viewpoint, gelatin is preferred. From viewpoints of eliminating animal origin infection such as bovine spongiform encephalopathy (BSE), avoiding ingestion of animal origin substances for religious reasons, and the like, substances derived from seaweed, substances derived from plant seeds, cellulose and starch are preferred, substances derived from seaweed and starch are more preferred, carrageenan and starch are still more preferred. From the viewpoint protecting reduced coenzyme $Q_{10}$ against oxidization even when the environment on preserving the preparation obtained is highly humid, carragheenan is particularly preferred. Needless to say, as the materials of the capsule, a combination of a plurality of species may be used, and a combination of carragheenan and starch is preferred.

In the preservation method of the present invention, the capsule containing reduced coenzyme $Q_{10}$ obtained as mentioned above is preserved in the surrounding environment controlled to a relative humidity of not less than about 0% but not more than about 60%.

The relative humidity is preferably not more than about 50%, more preferably not more than about 40%, still more preferably not more than about 30%, particularly preferably not more than about 20%, most preferably not more than about 10%. The lower limit value of the relative humidity of the environment controlled as mentioned above is 0%.

By preserving the capsule containing reduced coenzyme $Q_{10}$ in the above-mentioned environment, reduced coenzyme $Q_{10}$ in the capsule can be stably preserved.

In the present invention, such an environment controlled to a relative humidity of not more than 60% can be given, for example, by dehumidification from the environment; introduction of a dehumidified gas (preferably a dry inert gas such as dry nitrogen gas) into the environment; and the like. The method of dehumidification is not particularly restricted but the dehumidification may be accomplished by the freezing of moisture or the use of a dehumidifier or a desiccant (e.g. silica gel), and the like. It goes without saying that if an environment with a relative humidity of not more than 60% is given, the method for creating the same does not matter in any way.

In the present invention, the temperature at which the capsule containing reduced coenzyme $Q_{10}$ is preserved is not particularly restricted but, from the viewpoint of stability of a capsule outer cover, and the like, it is generally 60° C. or less, preferably 40° C. or less, more preferably 30° C. or less, still more preferably 25° C. or less. The lower limit of the above-mentioned preservation temperature is generally DOC, preferably 5° C., more preferably 10° C., still more preferably 15° C. Generally, it can be preserved suitably at ordinary temperature.

The preservation method of the present invention can be carried out at ordinary pressure, under increased pressure or under reduced pressure, and generally at ordinary pressure.

In the present invention, the control of the relative humidity in the environment surrounding the capsule is preferably carried out, for example, by packaging or packing this capsule containing reduced coenzyme $Q_{10}$ with packaging materials, and the like.

As the packaging materials, ones which substantially do not allow air circulation are preferred, and there may be mentioned, for example, films, pots, bottles and the like made from plastics such as polyethylene and polyethylene terephthalate (PET), glass and the like materials. In addition, metal (e.g. aluminum) film-based materials manufactured by lamination with plastic films can also be used.

The packaging and packing can be carried out by any packaging and packing means provided that the relative humidity of internal environment can be maintained to be not less than 0% but not more than 60%. More specifically, there may be mentioned packaging or packing, for example, sealing and the like, so that there may be substantially no air circulation, preferably substantially no moisture circulation.

In the case of packaging/packing using plastic films, aluminum laminated films and/or the like, it is also possible to carry out PTP packaging, three side-sealed packaging, four side-sealed packaging, pillow packaging, strip packaging, shaped packaging, stick packaging or the like. Two or more of these types of packaging may be used in combination. (For example, PTP-packed capsule is can be further packed with aluminum lamination pillow packaging and the) like.

According to need or preferably, a desiccant can be enclosed in such a packaging/packing. As the desiccants, there may be mentioned, for example, silica gel, calcium chloride, calcium oxide, a molecular sheave and the like.

After packaging/packing, the packages/packs obtained can be enclosed, according to need or preferably, in a steel drum, fiber drum, corrugated fiber board box or like container.

In the preservation method of the present invention, the packaging/packing of the capsule is preferably carried out in the environment with a relative humidity of not less than about 0% but not more than 60%. When packaging/packing is carried out in the environment with a relative humidity of higher than 60%, the environment with a relative humidity of not more than about 60% in the container can be achieved by enclosing the above-mentioned desiccants together as a drying agent in the container. It is of course possible to enclose the above-mentioned desiccants together when packaging/packing is carried out in the environment with a relative humidity of not more than about 60%.

The preservation method of the capsule containing reduced coenzyme $Q_{10}$, of the present invention, is preferred because it is able to increase its antioxidant effect by being carried out in a deoxygenated atmosphere. A deoxygenated atmosphere can be achieved by replacement with an inert gas, pressure reduction, or combinations of these. At least, replacement with an inert gas, that is, the use of an inert gas environment, is suitable. Examples of said inert gas include nitrogen gas, helium gas, argon gas, hydrogen gas, carbon dioxide gas, or the like, and nitrogen gas is preferable.

By using the preservation method of the present invention, reduced coenzyme $Q_{10}$ in a capsule is maintained stably. The weight ratio of reduced coenzyme $Q_{10}$/oxidized coenzyme $Q_{10}$ (reduced coenzyme $Q_{10}$ retention percentage) after pre-determined period of preservation is generally not lower than about 70%, preferably not lower than about 80%, more preferably not lower than about 90%, still more preferably not lower than about 93%, particularly preferably not lower than about 95%, more particularly preferably not lower than about 97%, most preferably not lower than about 98% assuming the weight ratio of reduced coenzyme $Q_{10}$/oxidized coenzyme $Q_{10}$ on encapsulation to be 100%.

In the preservation method of the present invention, what is necessary is just to make the relative humidity of the environment directly surrounding the capsule containing reduced coenzyme $Q_{10}$ be not less than 0% but not more than 60%. For example, the packed object which packs the capsule and is controlled inside thereof to a relative humidity of not more than 60% makes it possible to preserve reduced coenzyme $Q_{10}$ stably even when this packed object is placed in the environment with a relative humidity of higher than 60%, The packed object of the present invention is characterized in that a gas controlled to a relative humidity of not less than 0% but not more than 60% and the capsule containing reduced coenzyme $Q_{10}$ are packaged or packed in the packing material.

The gas referred herein may be any gas as long as being in a gas state under the preservation condition. And, this gas is not particularly restricted provided that the relative humidity of internal environment can be maintained to be not less than 0% but not more than 60%.

Preferably, the packaging material further packages or packs a desiccant therein.

According to the method of the present invention, reduced coenzyme $Q_{10}$ can be preserved stably, without requiring huge cost and labor, or special equipment.

BEST MODE FOR CARRYING OUT THE INVENTION

The following examples illustrate the invention in further detail. These examples are, however, by no means limitative of the scope of the invention.

The purity of reduced coenzyme $Q_{10}$ and weight ratio between reduced coenzyme $Q_{10}$ and oxidized coenzyme $Q_{10}$ in these examples were determined by the following HPLC analysis. The purity of reduced coenzyme $Q_{10}$ obtained is by no means regulative of the limit of the purity in the present invention. Similarly, the ratio of reduced coenzyme $Q_{10}$ in the weight ratio between reduced coenzyme $Q_{10}$ and oxidized coenzyme $Q_{10}$ is by no means regulative of the upper limit of the ratio in the present invention.

(HPLC Analysis Conditions):

Column: SYMMETRY C18 (product of Waters Corporation), 250 mm (length), 4.6 mm (inner diameter); mobile phase: $C_2H_5OH:CH_3OH=4:3$ (v:v); detection wavelength: 210 nm; flow rate: 1 ml/min.; retention time for reduced coenzyme $Q_{10}$: 9.1 min., retention time for oxidized coenzyme $Q_{10}$: 13.3 min.

Production Example 1

To 1,000 g of ethanol was added 100 g of oxidized coenzyme $Q_{10}$ and 60 g of L-ascorbic acid. These were stirred at 78° C., and a reduction reaction was carried out. After the lapse of 30 hours, the mixture was cooled to 50° C. and, while maintaining that temperature, 400 g of ethanol was added. The resulting ethanol solution (containing 100 g of reduced coenzyme $Q_{10}$) was cooled to 2° C. at a rate of about 10° C./hour with stirring (power required for stirring per unit volume: 0.3 kW/m³) to give a white slurry. The resulting slurry was filtered under reduced pressure, the wet crystals were washed with cold ethanol, cold water and cold ethanol in that order (the temperature of the cold solvents used for washing being 2° C.) and, further, the wet crystals were dried under reduced pressure (20 to 40° C., 1 to 30 mm Hg) to give 95 g of dry white crystals. All the operations other than drying under reduced pressure were carried out in a nitrogen atmosphere. The weight ratio of reduced coenzyme $Q_{10}$/oxidized coenzyme $Q_{10}$ in the resulting crystals was 99.5/0.5, and the purity of reduced coenzyme $Q_{10}$ was 99.4%.

Production Example 2

The reduced coenzyme $Q_{10}$ crystal obtained in Production Example 1 was added the a mixture composed of rape seed oil, diglycerol monooleate (product of Riken Vitamin Co., Ltd., Poem DO-100V), hydrogenated oil, beeswax and lecithin to obtain, by general methods, a geratin soft capsule containing 30 mg of reduced coenzyme $Q_{10}$. This capsule consists of the following components.

| | |
|---|---|
| Reduced coenzyme $Q_{10}$ | 9.94% by weight |
| Oxidized coenzyme $Q_{10}$ | 0.06% by weight |
| (the weight ratio of reduced coenzyme $Q_{10}$/oxidized coenzyme $Q_{10}$ was 99.4/0.6) | |
| Diglycerol monooleate | 32.0% by weight |
| Rapeseed oil | 33.0% by weight |
| Hydrogenated oil | 17.0% by weight |
| Beeswax | 6.0% by weight |
| Lecithin | 2.0% by weight |

Example 1

The soft capsule containing reduced coenzyme $Q_{10}$ obtained in Production Example 2 was placed shielded from light, at 40° C.±5° C. and in a desiccator set to a relative humidity of the values shown in Table 1. The weight ratios of reduced coenzyme $Q_{10}$/oxidized coenzyme $Q_{10}$ in the gelatin soft capsule after 1 month are given in Table 1. As for the preservation at a relative humidity of 40%, the result obtained using the composition containing reduced coenzyme $Q_{10}$, before encapsulated in the soft capsule, is also shown.

TABLE 1

| Relative humidity | Shape | Weight ratio of reduced coenzyme Q10/oxidized coenzyme Q10 |
|---|---|---|
| 10% | Soft capsule | 99.3/0.7 |
| 40% | Soft capsule | 97.6/2.4 |
| 50% | Soft capsule | 96.8/3.2 |
| 60% | Soft capsule | 95.1/4.9 |
| 75% | Soft capsule | 71.5/28.5 |
| 40% | Composition | 51.9/48.1 |

Example 2

The soft capsule containing reduced coenzyme $Q_{10}$ obtained in Production Example 2 was placed shielded from light, at 25° C.±5° C. and in a desiccator set to a relative humidity of the values shown in Table 2. The weight ratios of reduced coenzyme $Q_{10}$/oxidized coenzyme $Q_{10}$ in the gelatin soft capsule after 1 month are given in Table 2.

TABLE 2

| Relative humidity | Weight ratio of reduced coenzyme Q10/oxidized coenzyme Q10 |
| --- | --- |
| 40% | 99.2/0.8 |
| 50% | 98.0/2.0 |
| 60% | 97.6/2.4 |

Example 3

The soft capsule containing reduced coenzyme $Q_{10}$ obtained in Production Example 2 was packed by packing shown in Table 3 in the environment shielded from light, at 20° C.±5° C. and with a relative humidity of 30 to 60%.

TABLE 3

| Packing |
| --- |
| Sealed in a glass pot |
| PTP packaging |
| PTP packaging and further aluminum pillow packaging |
| PTP packaging and further aluminum pillow packaging (silica gel is also enclosed) |
| Aluminum lamination three side-sealed packaging |

Example 4

The packed object of a soft capsule containing reduced coenzyme $Q_{10}$ obtained in Example 3 was placed shielded from light and in a constant temperature and humidity incubator set to a temperature of 40° C.±5° C. and a relative humidity of 75%. The weight ratios of reduced coenzyme $Q_{10}$/oxidized coenzyme $Q_{10}$ in the gelatin soft capsule after 2 months are given in Table 4.

TABLE 4

| Packing | Weight ratio of reduced coenzyme Q10/oxidized coenzyme Q10 |
| --- | --- |
| Sealed in a glass pot | 98.9/1.2 |
| PTP packaging | 97.6/2.4 |
| PTP packaging and further aluminum pillow packaging | 99.1/0.9 |
| PTP packaging and further aluminum pillow packaging (silica gel is also enclosed) | 99.4/0.6 |
| Aluminum lamination three side-sealed packaging | 99.0/1.0 |
| No packing | 38.0/62.0 |

Example 5

A packed object (internal relative humidity of 10%) encapsulating the soft capsule containing reduced coenzyme $Q_{10}$ obtained in Production Example 2 and silica gel was produced using aluminum lamination three side-sealed packaging in the environment at 20° C.±5° C. and with a relative humidity of 70%. This packed object was placed in a constant temperature and humidity incubator set to a temperature of 40° C.±5° C. and a relative humidity of 75%. The weight ratio of reduced coenzyme $Q_{10}$/oxidized coenzyme $Q_{10}$ in the soft capsule after 2 months was 99.3/0.7.

Production Example 3

The reduced coenzyme $Q_{10}$ crystal obtained in Production Example 1 was added the a mixture composed of rape seed oil, diglycerol monooleate (product of Riken Vitamin Co., Ltd., Poem DO-100V), hydrogenated oil, beeswax and lecithin to obtain, by general methods, a carragheenan/starch soft capsule containing 50 mg of reduced coenzyme $Q_{10}$. This capsule consists of the following components.

| | |
| --- | --- |
| Reduced coenzyme $Q_{10}$ | 9.94% by weight |
| Oxidized coenzyme $Q_{10}$ | 0.06% by weight |
| (the weight ratio of reduced coenzyme $Q_{10}$/oxidized coenzyme $Q_{10}$ was 99.4/0.6) | |
| Diglycerol monooleate | 32.0% by weight |
| Rapeseed oil | 33.0% by weight |
| Hydrogenated oil | 17.0% by weight |
| Beeswax | 6.0% by weight |
| Lecithin | 2.0% by weight |

Example 6

The soft capsule containing reduced coenzyme $Q_{10}$ obtained in Production Example 3 was placed into a glass pot in the environment at 25° C.±5° C. and with a relative humidity of 50%, and then this glass pot was sealed. This pot was preserved in a constant temperature and humidity incubator set to a temperature of 40° C.±5° C. and a relative humidity of 75%. The weight ratio of reduced coenzyme $Q_{10}$/oxidized coenzyme $Q_{10}$ in a carragheenan/starch soft capsule after 1 month was 99.4/0.6.

Example 7

The soft capsule containing reduced coenzyme $Q_{10}$ obtained in Production Example 3 was placed shielded from light, at 40° C.±5° C. and in a desiccator set to a relative humidity of the values shown in Table 5. The weight ratios of reduced coenzyme $Q_{10}$/oxidized coenzyme $Q_{10}$ in a carragheenan/starch soft capsule after 1 month are given in Table 5.

TABLE 5

| Relative humidity | Weight ratio of reduced coenzyme Q10/oxidized coenzyme Q10 |
| --- | --- |
| 10% | 99.4/0.6 |
| 40% | 98.9/1.1 |
| 60% | 97.1/2.9 |
| 75% | 79.2/20.8 |

Example 8

The soft capsule containing reduced coenzyme $Q_{10}$ obtained in Production Example 3 was placed shielded from light, at 25° C.±5° C. and in a desiccator set to a relative humidity of the values shown in Table 6. The weight ratios of reduced coenzyme $Q_{10}$/oxidized coenzyme $Q_{10}$ in a carragheenan/starch soft capsule after 1 month are given in Table 6.

TABLE 6

| Relative humidity | Weight ratio of reduced coenzyme Q10/oxidized coenzyme Q10 |
| --- | --- |
| 40% | 99.4/0.6 |
| 50% | 99.4/0.6 |
| 60% | 98.6/1.4 |

The invention claimed is:

1. A method for preserving reduced coenzyme $Q_{10}$ which comprises producing or obtaining a capsule containing reduced coenzyme $Q_{10}$, and controlling environment surrounding the capsule to a relative humidity of not less than 0% but not more than 50% at a temperature in the range of 0° C. to 60° C. for preserving the reduced coenzyme $Q_{10}$,
wherein the control of the relative humidity is carried out by packaging or packing the capsule with a packaging material with a desiccant, and/or packaging or packing of the capsule in the environment controlled to a relative humidity of not less than 0% but not more than 50% at a temperature in the range of 0° C. to 60° C., and wherein the capsule containing reduced coenzyme $Q_{10}$ is preserved in the presence of molecular oxygen.

2. The method according to claim 1 wherein the content of reduced coenzyme $Q_{10}$ is not lower than 96% by weight relative to the whole weight of the coenzyme $Q_{10}$ used.

3. The method according to claim 1 wherein the capsule is a soft capsule, a hard capsule or a microcapsule.

4. The method according to claim 3 wherein the material of the capsule is at least one species selected from the group consisting of gelatin, carrageenan, alginic acid, locust bean gum, guar gum, starch and cellulose.

5. The method according to claim 4 wherein the material of the capsule is a combination of carrageenan and starch.

6. The method according to claim 1 wherein the desiccant is at least one species selected from the group consisting of silica gel, calcium chloride, calcium oxide and a molecular sieve.

7. The method according to claim 1 wherein the packaging or packing is at least one species selected from the group consisting of a bottle, press-through package, three side-sealed packaging, four side-sealed packaging, pillow packaging, strip packaging, shaped packaging and stick packaging.

8. The method according to claim 1, wherein a weight ratio of reduced coenzyme $Q_{10}$/oxidized coenzyme $Q_{10}$ after a predetermined period of preservation is not lower than 97% assuming the weight ratio of reduced coenzyme $Q_{10}$/oxidized coenzyme $Q_{10}$ on encapsulation to be 100%.

9. The method according to claim 8, wherein the predetermined period of preservation is one month.

10. The method according to claim 1, wherein reduced coenzyme $Q_{10}$ is preserved at ordinary pressure.

11. The method according to claim 1, wherein reduced coenzyme $Q_{10}$ is preserved at a temperature of 0° C. or higher.

* * * * *